United States Patent
Hebgen et al.

(10) Patent No.: US 6,680,416 B1
(45) Date of Patent: Jan. 20, 2004

(54) SUPPORTED CATALYST CONTAINING PSEUDO-BOEHMITE AND γ-$AL_2O_3$, PRODUCTION OF SAME AND ITS USE FOR PRODUCING 1,2-DICHLOROETHANE

(75) Inventors: Werner Hebgen, Heidelberg (DE); Christopher William Rieker, Ludwigshafen (DE); Ruprecht Meissner, Weisenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/646,003

(22) PCT Filed: Mar. 19, 1999

(86) PCT No.: PCT/EP99/01826

§ 371 (c)(1), (2), (4) Date: Sep. 11, 2000

(87) PCT Pub. No.: WO99/48606

PCT Pub. Date: Sep. 30, 1999

(30) Foreign Application Priority Data

Mar. 23, 1998 (DE) .......................... 198 12 468

(51) Int. Cl.[7] .......................... C07C 19/00; B01J 23/00; B01J 23/70; B01J 23/02
(52) U.S. Cl. .................. 570/245; 502/345; 502/346; 502/341; 502/302
(58) Field of Search ................... 502/302, 341, 502/345, 346; 570/245

(56) References Cited

U.S. PATENT DOCUMENTS

| | | | |
|---|---|---|---|
| 4,740,644 A | * 4/1988 | Eichhorn et al. | 570/245 |
| 5,175,382 A | * 12/1992 | Hebgen et al. | 570/221 |
| 5,696,309 A | * 12/1997 | Jackson et al. | 570/177 |
| 5,707,921 A | * 1/1998 | Wu et al. | 502/334 |

FOREIGN PATENT DOCUMENTS

| | | | | |
|---|---|---|---|---|
| DE | 3334223 A | * | 4/1985 | C07C/19/45 |
| DE | 4311650 A1 | * | 10/1994 | C04B/35/10 |
| EP | 0240714 A | * | 10/1987 | B01J/27/122 |

* cited by examiner

Primary Examiner—Wayne A. Langel
Assistant Examiner—Jonas N. Strickland
(74) Attorney, Agent, or Firm—Oblon, Spivak, McClelland, Maier & Neustadt, P.C.

(57) ABSTRACT

A process for preparing 1,2-dichloroethane by reacting about 2 mols of ethylene, about 4 mols of hydrogen chloride and about 1 mol of oxygen in the presence of a fixed bed of supported catalyst based on copper(II) chloride in only one reaction zone at a pressure of from 2 to 10 bar and at from 220 to 280° C., separating off 1,2-dichloroethane and water from the reaction mixture emerging from the reaction zone and passing most of the exhaust gas back into the reaction zone, where, prior to entry into the reaction zone, the exhaust gas is mixed with ethylene, hydrogen chloride and oxygen, and the oxygen content of the mixture does not exceed 7% by volume, and where the ethylene content of the gas mixture entering into the reaction zone is regulated so that the exhaust gas comprises less than 20% by volume of ethylene, where the supported catalyst used is obtained by tableting a mixture of pseudoboehmite and γ-$Al_2O_3$ in a weight ratio from 4:1 to 1:4, if desired with addition of tableting auxiliaries, loading this support with the active components by saturating with a $CuCl_2$/KCl solution so that the copper content is from 1 to 15% by weight and the potassium content is from 0.1 to 8% by weight, based in each case on the total weight of the catalyst, and then drying the catalyst at from 60 to 400° C.

13 Claims, No Drawings

SUPPORTED CATALYST CONTAINING PSEUDO-BOEHMITE AND γ-AL$_2$O$_3$, PRODUCTION OF SAME AND ITS USE FOR PRODUCING 1,2-DICHLOROETHANE

The present invention relates to a supported catalyst for preparing 1,2-dichloroethane by reacting about 2 mols of ethylene, about 4 mols of hydrogen chloride and about 1 mol of oxygen in the presence of a fixed bed of supported catalyst based on copper(II) chloride and potassium chloride on a support material based on aluminum oxide.

The invention further relates to the use of this supported catalyst for preparing 1,2-dichloroethane.

The preparation of 1,2-dichloroethane (EDC) is an intermediate step in the preparation of monomeric vinyl chloride. To this end, ethylene, hydrogen chloride and oxygen or an oxygen-containing gas are reacted, mostly in a stoichiometric ratio, using supported catalysts which comprise copper (II) chloride as active component. This process is also termed oxychlorination. Two particular processes have been introduced industrially, either with the catalyst arranged as a fixed bed or operating the reaction in a fluidized bed.

The fluidized-bed process for preparing EDC permits good heat dissipation, allowing high amounts of conversion per unit of catalyst by volume, at relatively low process temperatures. A disadvantage of this process is that there can be agglomeration of the catalyst particles and breakdown of the fluidized bed. In addition, a precipitation reaction is needed in this process in order to free the water of reaction from copper ions deriving from the catalyst dust entrained in the discharge.

The fixed bed process avoids all of the disadvantages of the fluidized bed process, but problems arise with heat flux and control of reaction temperatures. There are known, substantively one-stage, processes in which the reaction partners for preparing EDC are reacted in one reaction zone, and also three-stage processes with three reaction zones in which oxygen and, if desired, other reaction participants are introduced not only at the inlet of the first reaction zone but also at the inlet of the other reaction zones. This avoids the use of ignitable oxygen contents in the mixtures made from ethylene, hydrogen chloride and oxygen. However, a disadvantage of three-stage processes of this type is the relatively complicated and costly equipment required.

The disadvantages of the fixed-bed process are more markedly apparent in the single-stage processes, and therefore complicated activity-profile arrangements for the catalyst bed have been used in attempts to maintain balanced temperatures in the reaction zone.

DE-A-33 34 223 describes a process for preparing EDC with pure oxygen and exhaust gas recirculation. In this process the ethylene content of the gas mixture entering the reaction zone is regulated in such a way that the exhaust gas comprises less than 20% by volume of ethylene. This gives a good yield of 1,2-dichloroethane, based on the ethylene used and on the hydrogen chloride, and since only one reaction zone is used, i.e. one reactor, there is no requirement for complicated or costly equipment. A similar process is described in EP-A 240 714.

The supported catalysts used in DE-A-33 34 223 and EP-A-240 714 comprise Al$_2$O$_3$ as support material. However, Al$_2$O$_3$ is known in a variety of modifications which differ markedly in their structure and their mechanical properties, and with respect to their suitability as a support material for oxychlorination catalysts. Catalysts based on Al$_2$O$_3$ are generally unsatisfactory either with respect to their mechanical load-bearing capacity and abrasion resistance or with respect to their productivity and selectivity.

It is an object of the present invention, therefore, to provide a supported catalyst which has good productivity and selectivity in the preparation of 1,2-dichloroethane, together with good abrasion resistance.

We have found that this object is achieved by the supported catalyst as claimed in claim 1.

An appropriate way to prepare 1,2-dichloroethane is to introduce stoichiometric amounts of the reaction participants, i.e. ethylene, hydrogen chloride and oxygen, to the mixing system, i.e. to mix ethylene, hydrogen chloride and oxygen in a ratio such that for about 1 mol of oxygen about 2 mols of ethylene and about 4 mols of hydrogen chloride are used. This is intended to mean that the amounts may vary within the range ±10% of the molar amount given. In the novel process, therefore, the exhaust gas, i.e. the non-condensible process gases, which comprise less than 20% by volume of ethylene, in particular from 0.1 to 5% by volume of ethylene, and also some oxygen, mostly from 0.5 to 1.5% by volume, are admixed with the fresh gas whose composition is as above. Ethylene and hydrogen chloride are first mixed with the mixture in such a way that the volume of ignitable oxygen-containing mixture within the mixing apparatus is very small and the oxygen content of the homogeneous mixture is not higher than 7% by volume. This value is monitored continuously using an oxygen analyzer. The low oxygen content of the resultant mixture means that it is not ignitable under the reaction conditions. This entire mixture is then introduced into the reaction.

The ethylene content of the gas mixture entering the reaction zone is regulated so that the exhaust gas comprises less than 20% by volume of ethylene. For the purposes of the present invention, the exhaust gas is the non-condensible fractions of the reaction mixture after removal of the 1,2-dichloroethane and of the water. For this regulation, if there is a rise in the ethylene content of the exhaust gas, the amount of fresh ethylene in the ethylene stream is reduced, and if there is a fall-off to below 0.1% by volume the amount of fresh ethylene in the ethylene stream is increased. The amount of exhaust gas recirculated is adjusted as a function of its oxygen content, mostly between 0.5 and 1.5% by volume, so that the oxygen content continuously measured after mixing with the starting materials hydrogen chloride, ethylene and oxygen is maintained at 7% by volume.

In a procedure particularly advantageous for energy usage, the gas for the recirculation circuit is removed from the gaseous stream downstream of the water-cooled condensor, and it is then only a minor proportion of the exhaust gas discharged from the system which is passed through a brine cooler to condense further amounts of 1,2-dichloroethane and water. Surprisingly, the resultant recirculation gas produced at relatively high temperature and therefore relatively highly enriched in partial pressure terms with 1,2-dichloroethane and water has no adverse effect on the reaction.

In another particularly advantageous procedure, from 0.5 to 20% by volume of the exhaust gases is diverted and this diverted portion is passed through a carbon dioxide absorption column and is then passed back into the exhaust gas stream. This procedure further reduces ethylene losses in the process.

Further details concerning suitable apparatus for carrying out the oxychlorination reaction, and also concerning advantageous versions of the process, are described in DE-A-3334223.

The catalyst of the invention is based on a support which is prepared from a mixture of pseudoboehmite and γ-Al$_2$O$_3$. These two components are mixed with one another in fine-powder form, and the mixing ratio is from 4:1 to 1:4, preferably from 1:1 to 1:3. Tableting agents, which serve mainly as lubricants, are preferably added to the mixture. The skilled worker knows of many tableting auxiliaries of this type. Merely as examples, mention is made either of magnesium stearate and graphite. Magnesium stearate is preferably added in amounts of from 0.5 to 7% by weight, particularly preferably from 2 to 5% by weight, based on the total weight of the mixture. Graphite is generally added in amounts of from 0.5 to 3% by weight, preferably from 1 to 1.5% by weight.

The resultant mixture is then tableted. The mixture is preferably compressed into an annular or cylinder shape. The rings preferably have an external diameter of from about 5 to 7 mm, an internal diameter of from 2 to 3 mm and a height of from 3 to 8 mm, and the cylinders preferably have a diameter of from 3 to 7 mm and likewise a height of from 3 to 7 mm.

For the tableting the usual presses are used and the compressive force is preferably more than 9 kN, particularly preferably from 9 to 11 kN.

After tableting, the catalyst supports are calcined, generally for from 0.5 to 10 h at from 500 to 800° C., preferably for about 2 h at from 700 to 750° C. The calcination is undertaken in an oxidizing atmosphere, generally in air.

The tableting process described and the selection of the starting materials gives a catalyst support which firstly has good mechanical stability and secondly has an ideal pore volume for oxychlorination. The pore volume is sufficiently high to give a large internal surface for the active component. On the other hand, the pore volume is not excessively high, otherwise mechanical stability would be impaired and the bulk density achieved in the reactor would also not be ideal. The catalyst supports obtained according to the invention preferably have a pore volume of from 0.3 to 0.7 cm$^3$/g, particularly preferably from 0.4 to 0.6 cm$^3$/g.

The resultant support is then saturated with a $CuCl_2$/KCl solution. The saturation solution may also comprise HCl, and also salts of the elements Li, Na, Cs, Mg or Ca, and also those of the rare earth metals, preferably the chlorides of these elements. The pH of the saturation solution is preferably from 6 to 8.

The volume of the saturation solution is advantageously selected so that it is from 10 to 200% of the pore volume of the support, particularly preferably from 90 to 110%.

After the saturation, the catalyst pressings are dried, generally for from 0.2 to 10 h at from 80 to 300° C., preferably for from 0.5 to 2 h at from 100 to 200° C.

The concentration and the volume of the saturation solution are selected so that the supported catalyst has a Cu content of from 1 to 15% by weight, preferably from 2 to 10% by weight, and a K content of from 0.1 to 8% by weight, preferably from 0.3 to 3% by weight. If other elements from the abovementioned group are also applied to the support, the ratio between Cu and the total of other elements should be from 1.0 to 10 mol/mol, preferably from 1.1 to 6 mol/mol. The same figures are preferred for the ratio Cu:K. The activity profile of the catalyst preparation can be adjusted as desired via the selection of the metal concentrations in the catalyst, and also, if desired, by diluting with inert material, such as $Al_2O_3$. The supported catalyst obtained in this way has excellent suitability for use in the process for preparing 1,2-dichloroethane by oxychlorination. It combines excellent productivity and selectivity with good mechanical load-bearing capacity, and thus permits long operating times.

The examples below illustrate the invention.

EXAMPLES

Preparation of the Support Tablets

A dry mixture of 6 kg of gamma-alumina (Puralox SCF a230, Condea), 4 kg of pseudoboehmite (Pural SCF, Condea), 324 g of magnesium stearate and 100 g of graphite was compressed to a lateral compressive strength of 25 N for the tablets using a Kilian (model LX 18) tablet press to give annular tablets of dimensions 5×5×2 mm (height×external diameter×internal diameter). The tablets were then calcined in a normal atmosphere of air for 2 hours at 700° C. The resultant tablets had the following physical properties:

Weight per liter: 705 g/l
Water absorption: 0.51 ml/g
Lateral compressive strength: 33 N
BET surface area: 200 m$^2$/g
weight loss on ignition at 900° C.: 4.0% by weight Preparation of the Supported Catalyst For charging the reactor, catalyst types of diffeent activity were prepared by saturating the support tablets with aqueous $CuCl_2$/KCl solutions of different composition. The $CuCl_2$ concentration of the saturation solution was adjusted so that the copper contents obtained in the catalysts were from 1.7 to 5.5% by weight. The comparative catalyst was a support material according to DE-A-3334223 treated with the same saturation solutions.

Charging the Reactor

The catalyst prepared in a variety of activities was charged to the reactor in such a way that the copper content was 1.7% by weight at the reactor inlet and rose to 5.5% by weight at the reactor outlet.

Preparation of EDC

All of the experiments were carried out in an oxychlorination pilot plant. In all of the experiments the circulation gas, or the circulated exhaust gas, was first mixed with ethylene and HCl, followed by addition of oxygen. The oxygen content at the reactor inlet was about 7% or less. The gas mixture leaving the reactor was first cooled and partly condensed in a condenser which used water. After the condensed constituents (crude EDC and water) had been separated off, most of the uncondensed fraction was heated by about 10° C. and conveyed to the reactor inlet by means of a compressor. A smaller amount was passed at a regulated pressure (4.5 bar) through a cooler which used brine. The fractions condensed there were combined with the condensate downstream of the water condensor and the exhaust gas was led away. The temperatures in the reactor were from 180 to 270° C.

The comparative experiment 1c repeats the prior art of EP-A 240 714 and DE-A 33 34 223. The catalyst used had only gamma-alumina as support material. Experiments A, B and C are three independent experimental series and are inventive, i.e. the improved catalyst described above was used.

The attached tables give the EDC production, and also the conversions of ethene and HCl, as averages of a number of individual determinations. Each experiment took from 4 to 10 weeks. After 6 weeks the pressure rise, which can be attributed to catalyst abrasion, was measured.

Table 1 attached shows the advantages of the novel process over the comparative experiments, especially in higher productivity, and in reduced amounts of exhaust gas per unit and thus better ethene conversion. The improved catalyst has a lower combustion rate and improved abrasion resistance, which reduces the rise in pressure loss through the reactor.

TABLE 1

Results of experiments in EDC preparation with the novel catalysts

| Example | EDC productivity kg/h | Conversion % of ethene | Conversion % of HCl | Pressure rise in % after 6 weeks |
|---------|----------------------|------------------------|---------------------|----------------------------------|
| A       | 88.8                 | 99.9                   | 98.6                | 10.0                             |
| B       | 84.9                 | 99.9                   | 98.8                | 7.4                              |
| C       | 93.0                 | 99.9                   | 99.1                | 12.9                             |
| 1c      | 72.9                 | 99.8                   | 97.9                | 14.3                             |

We claim:

1. A supported catalyst for preparing 1,2-dichloroethane produced by
   a) preparing a pulverulent support material based on aluminum oxide,
   b) compressing said support material to form a tablet,
   c) calcining said support material for from 0.5 to 10 h at from 500 to 800° C.,
   d) saturating said support material with a $CuCl_2$/KCl solution so that the copper content is from 1 to 15% by weight and the potassium content is from 0.1 to 8% by weight, in each case based on the total weight of the catalyst,
   e) drying said supported catalyst at from 60 to 400° C.,
   wherein said support material comprises a mixture of $\gamma$-$Al_2O_3$ with pseudoboehmite in a weight ratio of from 4:1 to 1:4, optionally with addition of tableting auxiliaries.

2. The supported catalyst according to claim 1, wherein the ratio weight of pseudoboehmite and $\gamma$-$Al_2O_3$ in said mixture is from 1:1 to 1:3.

3. The supported catalyst according to claim 1, wherein said support material has a pore volume of from 0.3 to 0.7 $cm_3$/g.

4. The supported catalyst according to claim 1, wherein the Cu content of said supported catalyst is from 2 to 10% by weight.

5. The supported catalyst according to claim 1, wherein the K content of said supported catalyst is from 0.3 to 3% by weight.

6. The supported catalyst according to claim 1, wherein said supported catalyst comprises elements selected from the group consisting of Li, Na, Cs, Mg, Ca and the rare earth metals, in addition to the elements copper and potassium.

7. A process for preparing 1,2-dichloroethane comprising: reacting ethylene, hydrogen chloride and oxygen in the presence of the supported catalyst of claim 1.

8. A process for preparing 1,2-dichloroethane comprising:
   a) reacting about 2 mols of ethylene, about 4 mols of hydrogen chloride and about 1 mol of oxygen in the presence of the supported catalyst of claim 1 in one reaction zone at a pressure of from 2 to 10 bar and at a temperature of from 220 to 280° C.,
   b) separating 1,2-dichloroethane and water from the reaction mixture emerging from said reaction zone.

9. The process according to claim 8, wherein exhaust gas from said reaction mixture is passed back into said reaction zone with said ethylene, said hydrogen chloride and said oxygen.

10. The supported catalyst according to claim 1, wherein said calcining is for about 2 h at from 700 to 750° C.

11. The supported catalyst according to claim 1, wherein said support material has a pore volume from 0.4 to 0.6 $cm^3$/g.

12. The supported catalyst according to claim 1, wherein the ratio Cu:K is from 1.0 to 10 mol/mol.

13. The supported catalyst according to claim 1, wherein the ratio Cu:K is from 1.1 to 6 mol/mol.

* * * * *